(12) United States Patent
Spickermann et al.

(10) Patent No.: US 10,251,992 B2
(45) Date of Patent: Apr. 9, 2019

(54) CHAMBER FOR A BLOOD TREATMENT SYSTEM, BLOOD TUBING SYSTEM, AND BLOOD TREATMENT SYSTEM

(71) Applicant: Fresenius Medical Care Deutschland GmbH, Bad Homburg (DE)

(72) Inventors: Reiner Spickermann, Wasserlosen-Burghausen (DE); Gerhard Wiesen, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 135 days.

(21) Appl. No.: 14/575,275

(22) Filed: Dec. 18, 2014

(65) Prior Publication Data
US 2015/0182683 A1 Jul. 2, 2015

Related U.S. Application Data

(60) filed as application No. PCT/EP2010/003596 on Jun. 16, 2010, now abandoned.

(60) Provisional application No. 13/379,762.

(30) Foreign Application Priority Data

Jun. 24, 2009 (DE) .................. 10 2009 030 283

(51) Int. Cl.
*A61M 1/36* (2006.01)
*B01D 19/00* (2006.01)
*A61M 1/16* (2006.01)

(52) U.S. Cl.
CPC ........ *A61M 1/3627* (2013.01); *A61M 1/1601* (2014.02); *B01D 19/0031* (2013.01); *A61M 2205/7536* (2013.01)

(58) Field of Classification Search
CPC .............. A61M 1/3627; A61M 1/3628; A61M 1/1601; A61M 2205/7536; B01D 19/0031
See application file for complete search history.

(56) References Cited

U.S. PATENT DOCUMENTS

| | | | |
|---|---|---|---|
| 3,834,386 A | 9/1974 | Sisley | |
| 4,900,308 A * | 2/1990 | Verkaart | ............. A61M 5/36 604/126 |
| 5,330,425 A | 7/1994 | Utterberg | |
| 5,421,815 A | 6/1995 | Noguchi et al. | |
| 5,849,065 A * | 12/1998 | Wojke | ............. A61M 1/3627 96/211 |
| 5,858,239 A * | 1/1999 | Kenley | ............. A61M 1/3627 210/143 |
| 6,013,061 A * | 1/2000 | Kelley | ............. A61M 5/36 604/126 |
| 6,336,916 B1 | 1/2002 | Bormann et al. | |

(Continued)

FOREIGN PATENT DOCUMENTS

| | | |
|---|---|---|
| DE | 3202582 | 9/1982 |
| WO | WO 2004/000391 | 12/2003 |
| WO | WO 2007/050211 | 5/2007 |

*Primary Examiner* — Terry K Cecil
(74) *Attorney, Agent, or Firm* — Jacobson Holman, PLLC.

(57) ABSTRACT

A chamber for a blood treatment system having a blood inlet and a blood outlet, a filter element for air separation which is arranged at the head side with respect to the position of the chamber in the operating state, and which can be decoupled from the blood present in the chamber in the operating state via a further liquid.

19 Claims, 1 Drawing Sheet

(56) References Cited

U.S. PATENT DOCUMENTS

| | | |
|---|---|---|
| 7,871,391 B2 | 1/2011 | Folden et al. |
| 7,938,967 B2 * | 5/2011 | Folden ................ A61M 1/3627 210/323.1 |
| 8,142,383 B2 | 3/2012 | Dannenmaier et al. |

* cited by examiner

CHAMBER FOR A BLOOD TREATMENT SYSTEM, BLOOD TUBING SYSTEM, AND BLOOD TREATMENT SYSTEM

CROSS-REFERENCE TO RELATED APPLICATIONS

This application is a continuation of U.S. Application No. 13/379,762, filed Dec. 21, 2011, now abandoned, which is a national stage of PCT/EP2010/003596, filed Jun. 16, 2010.

BACKGROUND OF THE INVENTON

1. Field of Invention

The present invention relates to a chamber for a blood treatment system having a blood inlet and a blood outlet, and a filter element for air separation which is arranged at the head side with respect to the position of the chamber in the operating state and which can be decoupled from the blood present in the chamber in the operating state by means of a further liquid, to a blood hose system and to a blood treatment system.

2. Description of the Prior Art

In known hemodialysis systems a venous drip chamber which is a component of the extracorporeal blood circuit is located downstream of a dialysis filter. Said venous drip chamber provides a bubble-free reinfusion of the dialyzed patient blood at this point. The venous drip chamber is usually not completely filled. There is thus a disadvantageous blood-to-air contact here. To avoid an infusion of blood clots, the venous drip chamber is equipped with a clot trap which is as a rule designed as a screen.

A plurality of examples for drip chambers are already known from the prior art.

DE 32 02 582 A1, for instance, shows a drip chamber in which the blood dripping in does not drop directly into the blood level, but rather onto an oblique inner wall to minimize foam formation and thus the risk of a possible hemolysis.

U.S. Pat. No. 5,330,425 describes a plurality of blow-molded drip chambers for dialysis treatment having a specially located injection site.

U.S. Pat. No. 3,834,386 describes a drip chamber having a septum integrated into the cap of the drip chamber.

The blood inlet into the chamber frequently takes place in the state of the art via a corresponding port whose end is above the blood level. A dripping of the blood into the chamber therefore takes place, which brings along the danger of the formation of microbubbles, with such microbubbles not being able to be separated and being able to be led back to the patient without impediment. These microbubbles can moreover cause hemolysis.

A standard drip chamber usually furthermore has an injection port having a hydrophobic septum and has a venting line which is provided with a hydrophobic membrane, in particular a so-called transducer protector (TDP). The venting line can, on the one hand, be guided via a 3-way valve in the interior of the machine to a pressure transducer for the monitoring of the pressure in the venous drip chamber or can, on the other hand, vent the drip chamber via a pressure reducer, such as is the case on the initial filling of the hose system or of the extracorporeal blood circuit.

A venous drip chamber is furthermore known from WO 2007/050211 A2 in which the blood inlet port and the blood outlet port are arranged in the base of the chamber and wherein a dividing wall is located between the blood inlet port and the blood outlet port. A hydrophobic membrane is let into the cap of the chamber to vent the chamber. The chamber is completely filled with saline solution at the start, with the filling taking place via a blood inlet port. When blood is flowing into the chamber in dialysis operation, the displaced saline solution is supplied to the patient. A certain quantity of saline solution remains in the chamber to decouple the hydrophobic membrane from the blood level. The handling of such a drip chamber is often associated with not insignificant effort and considerable care since it has to be ensured that sufficient saline solution remains in the chamber to decouple the hydrophobic membrane from the blood level and to ensure a correct operation of the drip chamber.

SUMMARY OF THE INVENTION

It is therefore the object of the present invention to further develop in an advantageous manner a chamber for a blood treatment system of the initially named kind, in particular such that a venous drip chamber is provided which has minimized blood-to-air contact, which also reliably prevents the formation of microbubbles and can moreover be operated simply and reliably.

This object is solved in accordance with the invention by a chamber for a blood treatment system having the features described herein. Provision is accordingly made that a chamber for a blood treatment system has a blood inlet and a blood outlet as well as a filter element for air separation which is arranged at the head side with respect to the position of the chamber in the operating state by means of a further liquid. Provision is further made that the blood inlet is arranged at the head side. The advantage results due to the arrangement of the blood inlet at the head side that the simple handling capability can be maintained with the chamber in accordance with the invention, such as was also already the case with the previous drip chambers. For the blood inlet at the head side allows a simple filling of the chamber with blood. This is in particular of advantage on the initial venting of the drip chamber. The air separation is no longer carried out via a transducer protector due to the filter element for air separation arranged at the head side, but rather directly via a filter membrane which is decoupled from the blood by means of a further liquid so that a so-called clotting of blood at the filter element is prevented.

The chamber moreover advantageously no longer has a venting line. Consequently a wetting or a breakthrough of the advantageously no longer present transducer protector (TDP) can also not occur, whereby the danger of contaminating e.g. the connected dialysis machine is precluded.

A plurality of problems of the current extracorporeal circuit can thus be solved. It is possible to carry out a conversion of the pressure measurement to a non-invasive measurement by means of a pressure dome, for example, with a cessation of the transducer protector problems resulting. The contamination consequences at the machine side associated with the transducer protector furthermore no longer occur since, for example, a replacement of a pressure transducer after a blood contact no longer has to take place. Since there is no air present in the operating state of the chamber, since preferably the lower half is completely filled with blood and the further liquid which decouples the filter element from the blood present in the chamber in the operating state is located above the blood level, there is no direct blood-to-air contact and no stagnation regions in the chamber. The need for clotting inhibitors can thereby be considerably reduced. The formation of microbubbles in the venous chamber can furthermore be prevented.

Provision can be made that the blood outlet is arranged at the base side in the chamber with respect to the position of the chamber in the operating state.

The invention furthermore relates to a chamber for a blood treatment system having the features described herein. Provision is accordingly made that a chamber for a blood treatment system has a blood inlet and a blood outlet as well as s filter element for air separation which is arranged at the head side with respect to the position of the chamber in the operating state and which can be decoupled from blood present in the chamber in the operating state by means of a supply port. The advantage thereby results that the further liquid for the decoupling of the filter element from blood present in the chamber in the operating state can be supplied during operation. Liquid can thus optionally be topped up when some of the decoupling liquid mixes with the blood in the chamber and should thus leave the chamber through the blood outlet in operation.

Provision can be made that a chamber having the feature of a supply port has the characterizing features described above.

Provision can further be made that the chamber having the feature of the blood inlet being arranged at the head side has the characterizing feature of the aforementioned supply port.

It is furthermore conceivable that the further liquid can be supplied continuously or can be supplied at predefined time intervals and/or that the filter element includes a hydrophobic filter membrane or is formed by such. The advantage thereby results that it is ensured during operation that the filter element does not clog. It is in particular of advantage on the continuous supply of liquid that a continuous air separation is ensured due to the continuously onflowed hydrophobic membrane. It is hereby effectively avoided that blood components can collect at the hydrophobic membrane. The same effect can also be achieved in that the further liquid is supplied at predefined time intervals, for instance in a clocked manner. Air separation from the blood can then take place at the interface between the blood and the further liquid. The air rising out of the blood passes over the interface between blood and the further liquid and then rises upwardly. It can there escape via the hydrophobic filter. A mixing of blood and the further liquid can take place at the liquid boundary between the two substances, which is equivalent, for example, to a bolus addition on a hemofiltration or hemodiafiltration. In order advantageously to maintain the substitute level or the liquid level of the further liquid around the hydrophobic membrane, the substituate must be permanently topped up. This is preferably done via the setting of a substituate flow via the supply port and corresponding means for substituate control of e.g. a dialysis machine. In this process, the substituate introduced does not come into contact with air, unlike with drip chambers in which the substituate is dripped in via an infusion port. This avoids the formation of microbubbles and their infusion into the patient. The chamber is, for example, also suitable for hemodialysis when the introduced substituate quantity is small.

Provision can furthermore be made that the supply port has a check valve and/or a means preventing a backflow. The advantage hereby results that an inflow of blood into the supply port can be effectively prevented.

Provision can furthermore be made that the chamber has an infusion port and/or, in front of the blood inlet, a screen. The screen can, for example, be a so-called clot trap. It is possible in a simple manner by the infusion port to connect one or more infusions to the chamber.

It is furthermore conceivable that the chamber has a substantially cylindrical base body and the chamber is designed so eccentrically and/or flared in its upper end that the blood entering into the chamber via the blood inlet can be dripped onto an oblique wall formed thereby, with the blood inlet being arranged eccentrically and parallel to the center axis of the chamber so that the blood can be supplied to the chamber in an off-center manner. The advantage hereby results that the occurrence of microbubbles is further prevented since, on the one hand, foam formation can be effectively prevented on the initial filling. On the other hand, the path through the air of a blood droplet up to the impact on the wall is hereby reduced on the initial filling.

Provision can in particular be made that the blood inlet in the operating state is below the blood level adopted in operation with a filled chamber. This means that the outlet opening of the blood inlet is located beneath the blood level in the chamber and the blood supplied to the chamber can enter directly and without diversions or air contact into the blood compartment in the chamber.

Provision can furthermore be made that the outlet of the supply port for the substituate is arranged directly next to the filter element at the head side. The advantage thereby results that a simple and secure flow pattern around the filter element can be ensured.

Provision can moreover be made that the chamber is a venous drip chamber of a blood hose system, in particular of a blood hose system for dialysis.

It is furthermore conceivable that the liquid which can be supplied via the supply port is a filtered and pyrogen-free liquid, in particular a pyrogen-free and filtered dialysate and/or a saline solution.

The present invention furthermore relates to a blood hose system having the features described herein. Provision is accordingly made that a blood hose system is provided with at least one chamber as described herein.

The invention furthermore relates to a blood treatment system having the features described herein. Provision is accordingly made that a blood treatment system is provided with at least one chamber and/or a blood hose system as described herein.

Provision can be made that the blood treatment system is a dialysis machine and that the liquid which can be supplied via the supply port is filtered and pyrogen-free dialysate which is provided and/or treated by the dialysis machine.

BRIEF DESCRIPTION OF THE DRAWINGS

Further details and advantages will now be explained in more detail with reference to an embodiment shown in the drawing. There are shown.

DETAILED DESCRIPTION OF THE PREFERED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
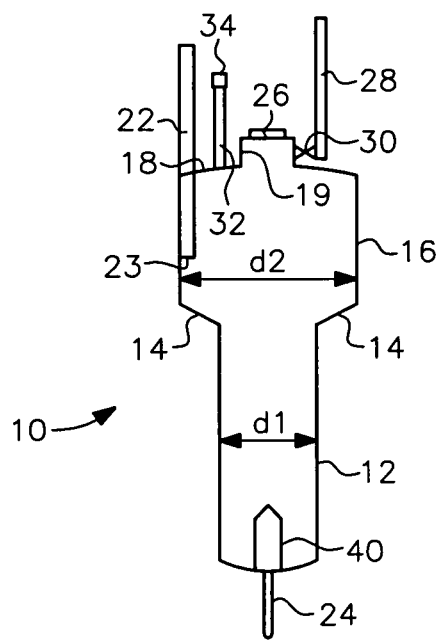
FIG. 1: a schematic representation of a chamber in accordance with the invention for a blood treatment system.
Figure 2:
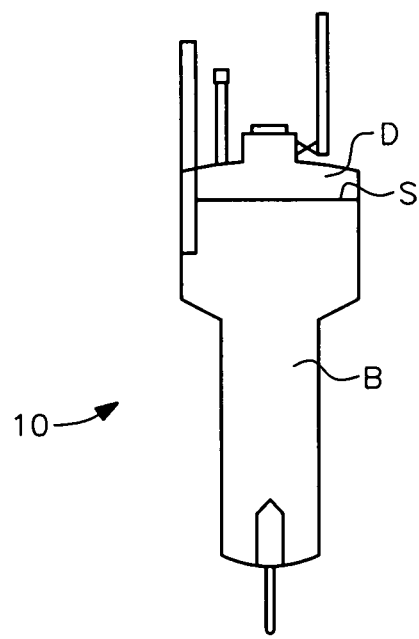
FIG. 2: a further schematic representation of the chamber shown in FIG. 1.

The blood inlet 22 is in this respect arranged eccentrically and parallel to the center axis of the chamber 10 so that the blood can be supplied to the chamber in an off-center manner. The blood inlet 22 is in this respect a rigid tubular piece 22 whose outlet opening, as shown in FIG. 2, is located beneath the blood level B adopted in the chamber 10 in the operating state. The blood inlet tubular piece 22 in this respect contacts the inner side of the wall of the upper region 16 which has a diameter d2. The diameter d2 is in this respect larger than the diameter d1, whereby it is ensured that the blood exiting the outlet opening 23 initially on the filling of the chamber 10 is dripped onto the slanted wall 14 and not onto the blood already present in the lower region 12. The dialysed blood entering into the chamber 10 leaves the chamber 10 after passing through the clot trap 40 which is arranged in front of the blood outlet 24 at the base side.

A dome-like molding 19 is provided centrally in the roof 18 of the chamber and the filter element 26 designed as a hydrophobic membrane 26 is arranged in its upper part. The air separation from the chamber is achieved via the filter element 26. This filter element 26 can optionally be a double membrane or have an additional filter such as a porous plastic filter, such as that commercially available under the trademark POREX ®, which can, for example, be of advantage with condensation effects.

In a preferred embodiment of the present invention, the filter element 26 is located above the outlet opening 23, and particularly preferred at the highest position in the chamber 10.

To ensure the continuous air separation over the total dialysis duration, the hydrophobic membrane 26 is washed by dialyzing liquid over the total dialysis duration which is supplied to the chamber via the supply port 28 with the check valve 30. The check valve 30 prevents blood from being able to enter into the supply line 28. The supply line 28 is connected to the dialysate line of the dialysis machine so that the pyrogen-free and filtered dialysate treated in the dialysis machine can be supplied continuously into the chamber during the dialysis duration via the supply port 28 so that the filter element 26 is constantly flushed.

The liquid distribution shown in FIG. 2 is adopted in this process, with the gas, in particular air, present in the blood B rising over the boundary surface S into the dialysate D or substituate D and moving from there to the air separator 26.

The chamber furthermore has an infusion port 32 which has a septum 34 or a luer connector 34.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A chamber for a blood treatment system, said chamber comprising:
   a blood inlet and a blood outlet;
   a roof provided at a top end of the chamber, the roof including a dome having a sidewall and a lower end fluidly connected with an interior of the chamber, with the dome being located axially atop the roof along a longitudinal axis of the chamber; and
   a filter element for air separation, said filter element being
      (i) arranged at the top end of the chamber with respect to a position of the chamber in an operating state thereof and
      (ii) decouplable during the operating state from blood (B) present in the chamber by a liquid (D) therein, with the blood inlet being arranged at the top end of the chamber and through the roof thereof, and with the filter element being located axially atop the dome at a highest point of the chamber.

2. The chamber in accordance with claim 1, wherein the blood outlet is arranged in the chamber at the bottom end with respect to the position of the chamber in the operating state.

3. The chamber in accordance with claim 1, wherein the liquid (D) is suppliable continuously or at predefined time intervals, and/or the filter element is a hydrophobic filter membrane, or includes a hydrophobic filter membrane.

4. The chamber in accordance with claim 1, further comprising a screen element arranged in front of the blood outlet.

5. The chamber in accordance with claim 1, wherein the chamber has a substantially cylindrical base body,
   the chamber is formed eccentrically and/or in a flared manner in an upper end thereof such that the blood entering into the chamber via the blood inlet is dripped on to an oblique wall formed thereby, with the blood inlet being arranged eccentrically and parallel to the longitudinal axis of the chamber so that the blood is supplied to the chamber in an off-center manner, and/or
   an outlet opening of the blood inlet is located beneath a blood level (S) present in the chamber during operation.

6. The chamber in accordance with claim 1, wherein the chamber is a venous drip chamber of a blood hose system.

7. The chamber according to claim 6, wherein the blood hose system is a dialysis blood hose system.

8. A blood hose system comprising at least one chamber in accordance with claim 1.

9. A blood treatment system comprising at least one chamber in accordance with claim 1.

10. The blood treatment system in accordance with claim 9, wherein the blood treatment system is a dialysis machine, and
   the liquid (D), which is supplied via a supply port, is a filtered and pyrogen-free dialysate which is at least one of provided by and treated by the dialysis machine.

11. A chamber for a blood treatment system, said chamber comprising:
   a blood inlet and a blood outlet;
   a roof provided at a top end of the chamber, the roof including a dome having a sidewall and a lower end fluidly connected with an interior of the chamber, with the dome being located axially atop the roof along a longitudinal axis of the chamber;
   a filter element for air separation, said filter element being
      (i) arranged at the top end of the chamber with respect to a position of the chamber in an operating state thereof and
      (ii) decouplable during the operating state from blood (B) present in the chamber by a liquid (D) therein; and
   a supply port via which the liquid (D) is supplied to the chamber,
   with the filter element being located axially atop the dome at a highest point of the chamber, and
   with the supply port being located in the sidewall of the dome, below and adjacent the filter element.

12. The chamber according to claim 11, wherein the blood inlet is arranged at the top end of the chamber.

13. The chamber in accordance with claim 11, wherein the supply port includes an element that prevents a backflow therein.

14. The chamber according to claim 13, wherein the element that prevents the backflow is a check valve.

15. The chamber in accordance with claim 11, wherein an outlet of the supply port is arranged in the dome directly next to the filter element.

16. The chamber in accordance with claim 11, wherein the liquid (D) which is supplied via the supply port is a filtered and pyrogen-free liquid.

17. The chamber according to claim 16, wherein the filtered and pyrogen-free liquid is at least one of a pyrogen-free and filtered dialysate, and a saline solution.

18. A chamber for a blood treatment system, said chamber comprising:
    a blood inlet and a blood outlet;
    a roof provided at a top end of the chamber, the roof including a dome having a sidewall, and a lower end fluidly connected with an interior of the chamber, with the dome being located axially in the roof along a longitudinal axis of the chamber;
    a filter element for air separation, said filter element being
        (i) arranged axially in the dome at a highest position of the chamber, above an outlet opening of the blood inlet, with respect to a position of the chamber in an operating state thereof and
        (ii) decouplable during the operating state from blood (B) present in the chamber by a liquid (D) therein; and
    a supply port in a side of the dome, via which the liquid (D) is supplied to the chamber.

19. The chamber according to claim 18, wherein the supply port is arranged in the dome to supply the liquid (D) such that the liquid (D) washes the filter element.

\* \* \* \* \*